(12) United States Patent
Polak

(10) Patent No.: US 8,521,297 B2
(45) Date of Patent: Aug. 27, 2013

(54) ARTIFACT CANCELLATION IN HYBRID AUDIO PROSTHESES

(75) Inventor: Marek Polak, Innsbruck (AT)

(73) Assignee: MED-EL Elektromedizinische Geraete GmbH, Innsburck (AT)

( * ) Notice: Subject to any disclaimer, the term of this patent is extended or adjusted under 35 U.S.C. 154(b) by 449 days.

(21) Appl. No.: 12/635,972

(22) Filed: Dec. 11, 2009

(65) Prior Publication Data
US 2010/0152814 A1     Jun. 17, 2010

Related U.S. Application Data

(60) Provisional application No. 61/121,696, filed on Dec. 11, 2008.

(51) Int. Cl.
*A61B 5/04*     (2006.01)
*A61N 1/18*     (2006.01)

(52) U.S. Cl.
USPC .......................................... 607/57; 600/559

(58) Field of Classification Search
USPC .................... 600/554, 559; 607/2, 55, 56, 57
See application file for complete search history.

(56) References Cited

U.S. PATENT DOCUMENTS

| | | | |
|---|---|---|---|
| 7,171,261 B1 | 1/2007 | Litvak et al. | 600/544 |
| 2006/0287690 A1 | 12/2006 | Bouchataoui et al. | 607/57 |

OTHER PUBLICATIONS

International Bureau of WIPO, Notification of International Preliminary Report with Written Opinion of International Searching Authority, PCT/US2009/067626, dated Jun. 14, 2011.

*Primary Examiner* — Allen Porter, Jr.
(74) *Attorney, Agent, or Firm* — Sunstein Kann Murphy & Timbers LLP

(57) ABSTRACT

A system and method are described for determining an estimated neural response in a hybrid acoustic-electrical audio prosthesis. Target nerve tissue such as remaining hair cells and cochlear nerve tissue receive synchronized electric and acoustic stimulation signals which are recorded and processed to determine an artifact canceled estimated neural response.

10 Claims, 7 Drawing Sheets

ARTIFACT CANCELLATION IN HYBRID AUDIO PROSTHESES

This application claims priority from U.S. Provisional Patent Application 61/121,696, filed Dec. 11, 2008, which is incorporated herein by reference.

FIELD OF THE INVENTION

The present invention relates to artifact cancellation in hybrid electric and acoustic stimulation audio prostheses.

BACKGROUND ART

Cochlear implants (CI) help profoundly deaf or severely hearing impaired persons to perceive environmental sounds. Unlike conventional hearing aids, which just apply an amplified and modified sound signal, a cochlear implant is based on direct electrical stimulation of the auditory nerve. The intention of a cochlear implant is to electrically stimulate nervous structures in the inner ear so that hearing impressions most similar to normal hearing are obtained.

A cochlear implant system includes an external speech processor and the implanted stimulator. The speech processor contains a power supply and is used to perform signal processing of the acoustic signal to extract stimulation parameters for the implanted stimulator. The implanted stimulator generates stimulation patterns and conducts them to auditory nervous tissue by an electrode array which usually is positioned in the scala tympani in the inner ear. A connection between the speech processor and the implanted stimulator can be established by encoding digital information in an rf-channel and coupling the signal transcutaneously using an inductive coupled coils arrangement. The information is decoded within the implanted stimulator by envelope detection of the rf signal.

Applying a stimulus pulse to nerve tissue creates an action potential. The period of time immediately after the action potential is referred to as the refractory period, during which the nerve tissue has not returned to its resting state and is not ready to respond to a second stimulus. The interval during which a second action potential absolutely cannot be initiated, no matter how large the applied stimulus, is known as the absolute refractory period. The interval after the absolute refractory period is known as the relative refractory period during which second action potential is inhibited but not impossible. The relative refractory period ends once the nerve tissue is ready to respond to another stimulus with a normal action potential.

Stimulation strategies employing high-rate pulsatile stimuli in multi-channel electrode arrays have proven to be successful in giving high levels of speech recognition. One example is the "Continuous Interleaved Sampling (CIS)"—strategy, as described by Wilson et al., *Better Speech Recognition With Cochlear Implants*, Nature, vol. 352:236-238 (1991), which is incorporated herein by reference. For CIS, symmetrical biphasic current pulses are used, which are strictly non-overlapping in time. The rate per channel typically is higher than 800 pulses/sec. Other stimulation strategies may be based on simultaneous activation of electrode currents.

For high-rate pulsatile stimulation strategies, some patient specific parameters typically need to be determined. This is done some weeks after surgery in a fitting procedure. For given phase duration of stimulation pulses and for given stimulation rate, two key parameters to be determined for each stimulation channel include:

1. the minimum amplitude of biphasic current pulses necessary to elicit a hearing sensation (Threshold Level, or THL); and
2. the amplitude resulting in a hearing sensation at a comfortable level (Most Comfort Level, or MCL).

For stimulation, only amplitudes between MCL and THL for each channel are used. The dynamic range between MCL and THL typically is between 6-12 dB. However, the absolute positions of MCLs and THLs vary considerably between patients, and differences can reach up to 40 dB. To cover these absolute variations, the overall dynamic range for stimulation in currently used implants typically is about 60 dB.

There are several methods of setting the MCLs and THLs. For example, they can be estimated during the fitting procedure by applying stimulation pulses and asking the patient about his/her subjective impression. This method usually works without problems with post-lingually deaf patients. However, problems occur with pre-lingually or congenitally deaf patients, and in this group all ages—from small children to adults—are concerned. These patients are usually neither able to interpret nor to describe hearing impressions, and only rough estimations of MCLs and THLs based on behavioral methods are possible. Especially the situation of congenitally deaf small children needs to be mentioned here. An adequate acoustic input is extremely important for the infant's speech and hearing development, and this input in many cases can be provided with a properly fitted cochlear implant.

One approach for an objective measurement of MCLs and THLs is based on the measurement of the EAPs (Electrically Evoked Action Potentials), as described by Gantz et al., *Intraoperative Measures of Electrically Evoked Auditory Nerve Compound Action Potentials*, American Journal of Otology 15 (2):137-144 (1994), which is incorporated herein by reference. In this approach, the recording electrode is usually placed at the scala timpani of the inner ear. The overall response of the auditory nerve to an electrical stimulus is measured very close to the position of the nerve excitation. This neural response is caused by the super-position of single neural responses at the outside of the axon membranes. The amplitude of the EAP at the measurement position is between 10 $\mu$V and 1800 $\mu$V. Information about MCL and THL at a particular electrode position can first of all be expected from the so called "amplitude growth function," as described by Brown et al., *Electrically Evoked Whole Nerve Action Potentials In Ineraid Cochlear Implant Users: Responses To Different Stimulating Electrode Configurations And Comparison To Psychophysical Responses*, Journal of Speech and Hearing Research, vol. 39:453-467 (June 1996), which is incorporated herein by reference. This function is the relation between the amplitude of the stimulation pulse and the peak-to-peak voltage of the EAP. Another interesting relation is the so called "recovery function" in which stimulation is achieved with two pulses with varying interpulse intervals. The recovery function as the relation of the amplitude of the second EAP and the interpulse interval allows conclusions to be drawn about the refractory properties and particular properties concerning the time resolution of the auditory nerve.

Besides cochlear implant systems as such, some subjects with some residual hearing (partial deafness) are now benefiting from combined electric and acoustic stimulation (EAS) such as was first described in von Ilberg et al., *Electric-Acoustic Stimulation Of The Auditory System*, ORL 61:334-340 (1999), which is incorporated herein by reference. EAS systems combine the use of a hearing aid (HA) device to provide acoustic-mechanical stimulation of lower audio frequencies to the subject's ear drum and a cochlear implant (CI) to provide intracochlear electrical stimulation of higher audio frequencies to the auditory nerve. For example, see Lorens et al., *Outcomes Of Treatment Of Partial Deafness With Cochlear Implantation: A DUET Study*, Laryngoscope, 2008 February: 118(2):288-94, which is incorporated herein by reference.

SUMMARY OF THE INVENTION

A system and method are described for determining an estimated neural response in a hybrid acoustic-electrical audio prosthesis. Target nerve tissue such as remaining hair cells and cochlear nerve tissue receive synchronized electric and acoustic stimulation signals which are recorded and processed to determine an artifact canceled estimated neural response.

In one specific embodiment, a control interface module determines an estimated neural response in a hybrid acoustic-electrical audio prosthesis. A recording is made of a B response by target nerve tissue to a first stimulus sequence. The first stimulus sequence includes delivering to the target nerve tissue a first stimulus pulse P1 to elicit a corresponding action potential followed by a relative refractory period, and after the relative refractory period, delivering to the target nerve tissue a second stimulus pulse P2 and an associated acoustic stimulation signal. A recording is also made of an E response by the target nerve tissue to a second stimulus sequence which includes delivering to the target nerve tissue a third stimulus pulse P3 to elicit a corresponding action potential followed by a relative refractory period, and within the relative refractory period, delivering to the target nerve tissue a fourth stimulus pulse P4. A recording is made of a C response by the target nerve tissue to delivery of a first reference stimulus pulse P5 corresponding to the first stimulus pulse P1. And a recording is made of a D response by the target nerve tissue to delivery of a second reference stimulus pulse P6 corresponding to the third stimulus pulse P3. The recorded responses are processed to determine an artifact canceled estimated neural response Y following the relation $Y=(B-C)-(E-D)$.

In further specific embodiments, the acoustic stimulation signal is triggered by the second stimulus pulse P2. The acoustic stimulation signal may precede or follow the second stimulus pulse P2. The pulses have substantially equal amplitudes, in which case, the recording of the D response may be a time shifted recording of the C response. The target nerve tissue may specifically be cochlear nerve tissue and hair cells, and the recordings may be based on measurements from cochlear implant electrodes.

In another specific embodiment, a control interface module determines an estimated neural response in a hybrid acoustic-electrical audio prosthesis. A recording is made of a B response by target nerve tissue to a first stimulus sequence which includes delivering to the target nerve tissue a first stimulus pulse P1 to elicit a corresponding action potential followed by a relative refractory period, and within the relative refractory period, delivering to the target nerve tissue a second stimulus pulse P2 and an associated acoustic stimulation signal. A recording is also made of an A response by the target nerve tissue to delivery of a first reference stimulus pulse P7 corresponding to the second stimulus pulse P2 and an associated acoustic stimulation signal. The acoustic stimulation signal may precede or follow the second stimulus pulse P2. A recording is made of a C response by the target nerve tissue to delivery of a second reference stimulus pulse P5 corresponding to the first stimulus pulse P1. The recorded responses are processed to determine an artifact canceled estimated neural response Y following the relation $Y=A-(B-C)$.

In further specific embodiments, the acoustic stimulation signal may be triggered by the second stimulus pulse P2. The acoustic stimulation signal may precede or follow the second stimulus pulse P2. The pulses may have substantially equal amplitudes. The target nerve tissue may be cochlear nerve tissue and hair cells, and the recordings may be based on measurements from cochlear implant electrodes.

In another specific embodiment, a control interface module determines an estimated neural response in a hybrid acoustic-electrical audio prosthesis. A recording is made of a B response by target nerve tissue to a first stimulus sequence which includes delivering to the target nerve tissue a first stimulus pulse P1 to elicit a corresponding action potential followed by a relative refractory period, and within the relative refractory period, delivering to the target nerve tissue a second stimulus pulse P2 and an associated acoustic stimulation signal. A recording is also made of an A response by the target nerve tissue to delivery of a first reference stimulus pulse P7 corresponding to the second stimulus pulse P2 and an associated acoustic stimulation signal. The acoustic stimulation signal may precede or follow the second stimulus pulse P2. A recording is made of a C response by the target nerve tissue to delivery of a second reference stimulus pulse P5 corresponding to the first stimulus pulse P1. A recording is made of an F response with a pair of reference stimulus pulses P8 and P9 associated with the first and second stimulus pulses P1 and P2. The recorded responses are processed to determine an artifact canceled estimated neural response Y following the relation $Y=A-(B-C)-F$.

In further specific embodiments, the acoustic stimulation signal may be triggered by the second stimulus pulse P2. The acoustic stimulation signal may precede or follow the second stimulus pulse P2. The pulses may have substantially equal amplitudes. The target nerve tissue may be cochlear nerve tissue and hair cells, and the recordings may be based on measurements from cochlear implant electrodes.

DETAILED DESCRIPTION OF SPECIFIC EMBODIMENTS

Embodiments of the present invention are directed to an objective measurement system for a hybrid electric and acoustic stimulation audio prosthesis which coordinates and synchronizes an acoustic stimulus and an electrical stimulus of remaining hair cells and neural cells, and the resulting evoked response is recorded and analyzed. This arrangement is especially useful in diagnostics of patients implanted with a hybrid electric and acoustic stimulation audio prosthesis (e.g., partial deafness) helping to optimize the fit for patients of their speech processor and the cochlear implant stimulation. These measurements can also be useful for identifying properties of the auditory nerve and higher levels of the auditory pathway and for acquiring information regarding the preservation of the remaining hearing in a patient.

Figure 1:
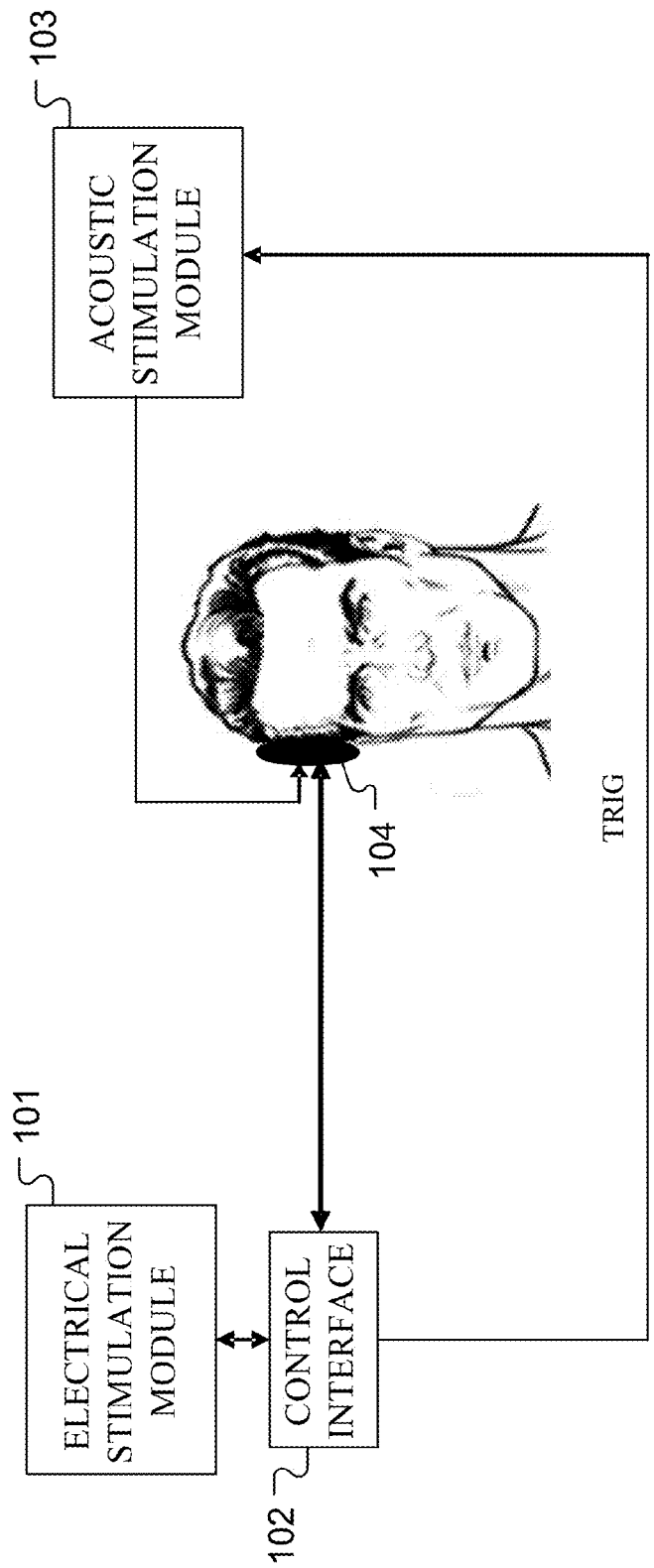
FIG. 1 shows various functional blocks in a system for determining an artifact canceled estimated neural response according to one specific embodiment of the present invention.

FIG. 1 shows various functional blocks in a system for determining an artifact canceled estimated neural response of a hybrid acoustic-electrical audio prosthesis according to one specific embodiment of the present invention. Electrical stimulation module 101 contains a combination of software and hardware for generating pulses for electrical stimulation of the target nerve tissue by the electrical portion of the prosthesis system. For example, electrical stimulation module 101 may be based on a Research Interface Box (RIB) II system manufactured at the University of Technology Innsbruck, Austria which may include a personal computer equipped with a National Instruments digital II card, a RIB II isolation box, and a communications cable between IO card and RIB II box. The electrical stimulation pulses are transmitted from the electrical stimulation module 101 through the control interface 102 to the audio prosthesis 104 which delivers them via the cochlear implant electrodes to the target nerve tissue. The electrical stimulation module 101 also includes software for recording near field responses from the cochlear implant electrodes. The electrical stimulation module 101 also provides a trigger to an acoustic stimulation module 103 which delivers acoustic stimuli to the audio prosthesis 104 for delivery via ear canal inserts to the middle ear. For example, the acoustic stimulation module 104 may be a Nicolet Spirit 2000 from Nicolet Biomedical Inc.

Figure 2:
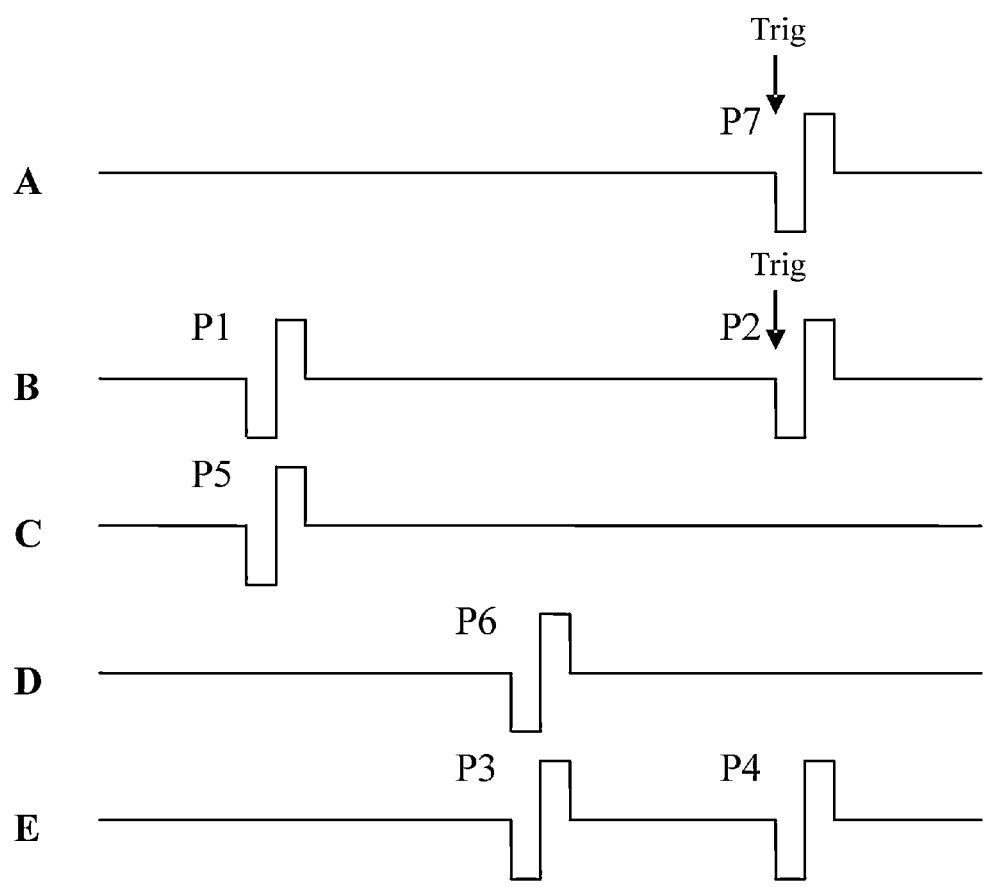
FIG. 2 shows a pulse stimulus paradigm according to an embodiment.
Figure 3:
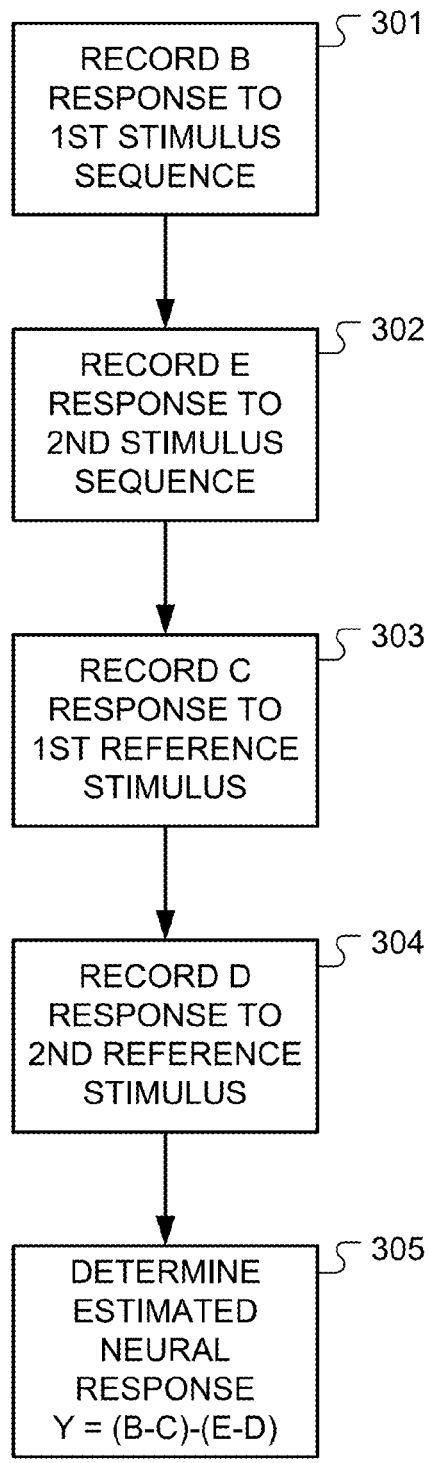
FIG. 3 shows various functional blocks in a method according to one embodiment.

FIG. 2 shows an example of a pulse stimulus paradigm and FIG. 3 shows various functional blocks in a method according to one embodiment. First, a recording is made of a B response by target nerve tissue to a first stimulus sequence, step 301. As shown in FIG. 2, the first stimulus sequence for the B response delivers a first stimulus pulse P1 that elicits a corresponding action potential followed by a relative refractory period. After the relative refractory period follows a second stimulus pulse P2 and an associated acoustic stimulation signal, step 302. The acoustic stimulation signal may specifically be triggered by the second stimulus pulse P2 and may precede or follow it. A recording is also made of an E response to a second stimulus sequence based on a third stimulus pulse P3 that elicits a corresponding action potential followed by a relative refractory period, within which a fourth stimulus pulse P4 is delivered. A recording is made of a C response by the target nerve tissue to delivery of a first reference stimulus pulse P5 corresponding to the first stimulus pulse P1, step 303. And a recording is made of a D response by the target nerve tissue to delivery of a second reference stimulus pulse P6 corresponding to the third stimulus pulse P3, step 304. All the pulses may have substantially equal amplitudes, in which case, the recording of the D response may usefully be a time shifted recording of the C response. The recorded responses are processed to determine an artifact canceled estimated neural response Y following the relation Y=(B−C)−(E−D), step 305.

Figure 4:
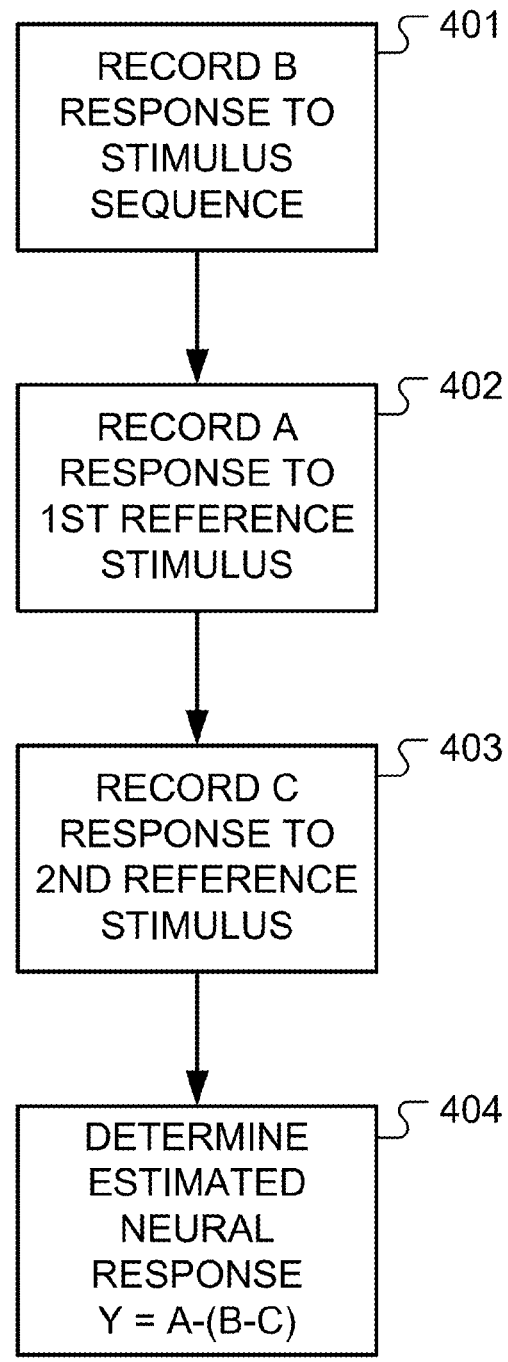
FIG. 4 shows various functional blocks in a method according to another embodiment.

FIG. 4 shows various functional blocks in another method of using the pulse stimulation paradigm of FIG. 2. In this embodiment, a first recording is made of a B response by target nerve tissue to a first stimulus sequence, step 401, which includes delivering to the target nerve tissue a first stimulus pulse P1 to elicit a corresponding action potential followed by a relative refractory period, and after the relative refractory period, delivering to the target nerve tissue a second stimulus pulse P2 and an associated acoustic stimulation signal. A recording is also made of an A response by the target nerve tissue to delivery of a first reference stimulus pulse P7 corresponding to the first stimulus pulse P2 and an associated acoustic stimulation signal, step 402. As before, the acoustic stimulation signal may specifically be triggered by the second stimulus pulse P2 and may precede or follow it. A recording also is made of a C response by the target nerve tissue to delivery of a second reference stimulus pulse P5 corresponding to the first stimulus pulse P1, step 403. The recorded responses then are processed to determine an artifact canceled estimated neural response Y following the relation Y=A−(B−C), step 404.

Figure 5:
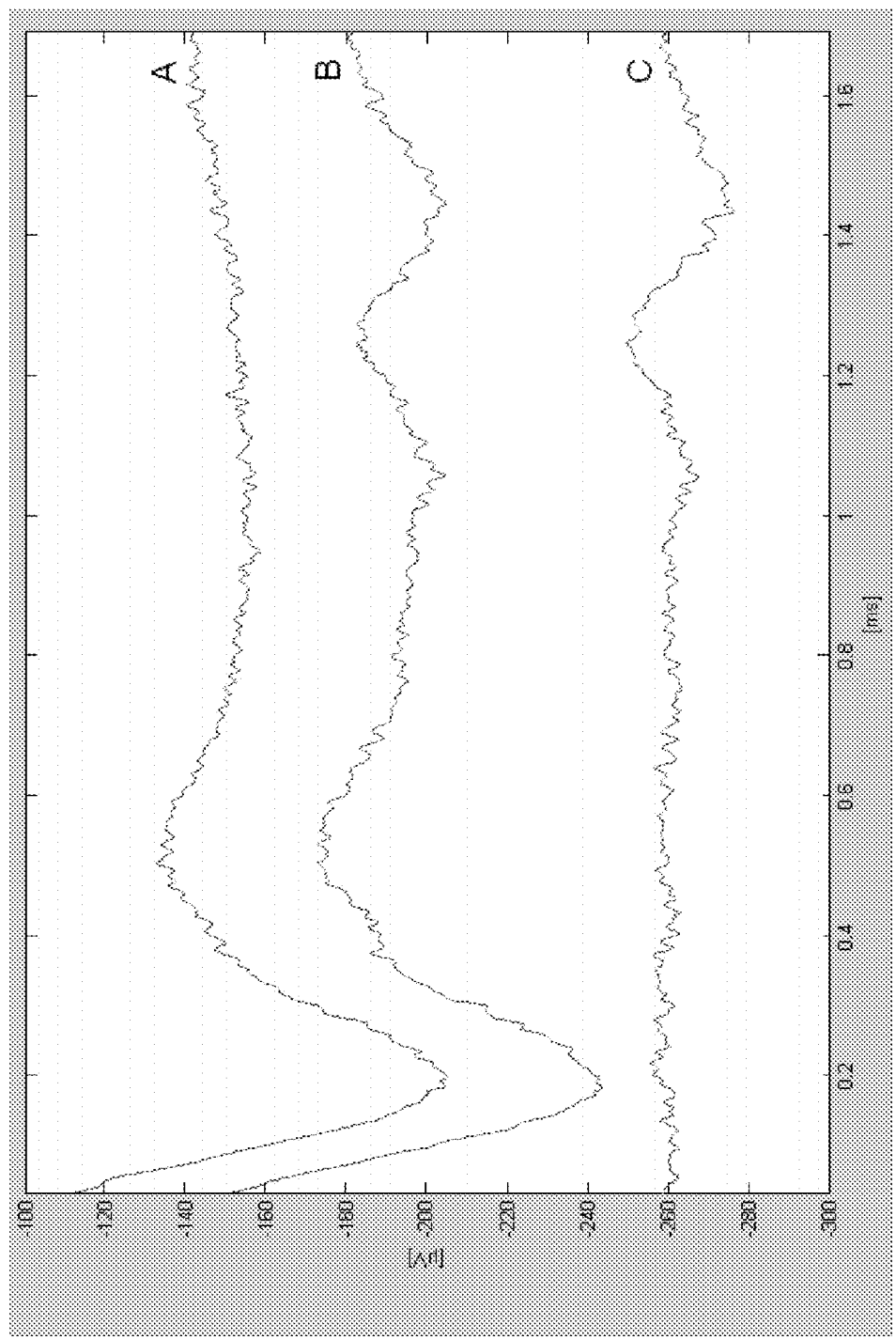
FIG. 5 shows an example of response recordings made according to an embodiment.

FIG. 5 shows an example of response recordings made according to an embodiment using the electric and acoustic stimulation to create evoked action potentials.

FIG. 5 specifically shows near field recordings from the cochlear implant stimulation electrodes. In the example shown, stimulation was at the most comfortable level of acoustic and electric stimuli where Waveform A shows the electrical stimulation only, Waveform B shows the combined acoustic and electrical stimulation, and Waveform C shows only the acoustic stimulation.

Figure 6:
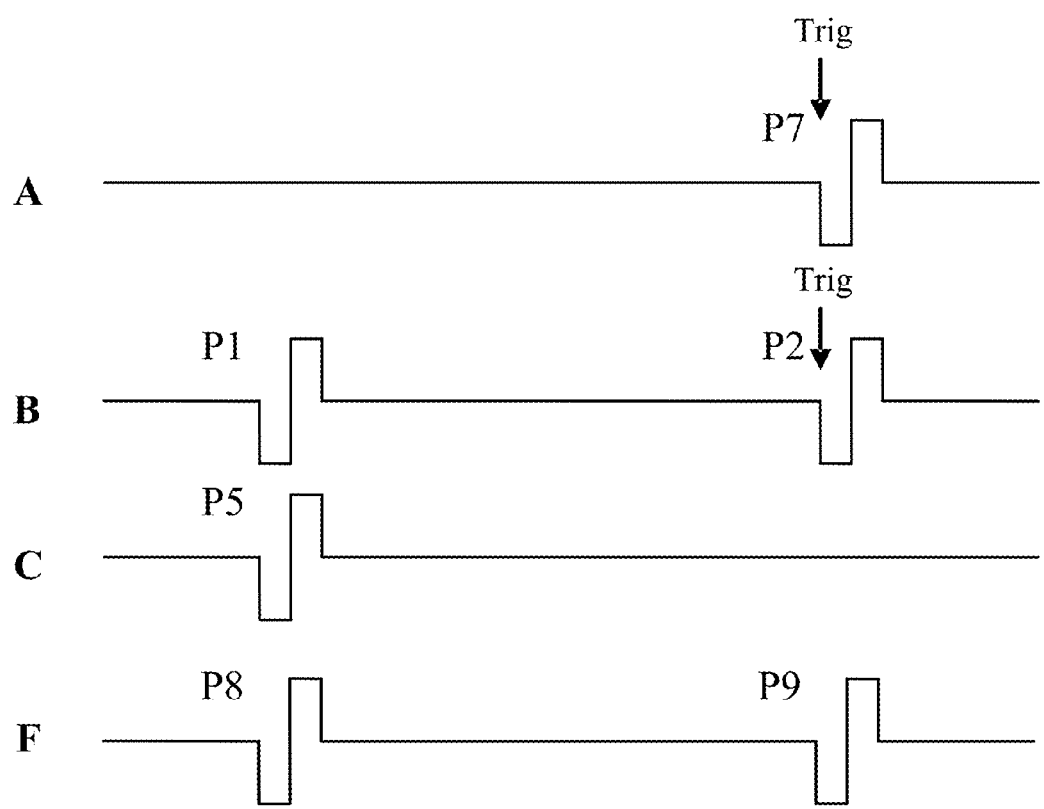
FIG. 6 shows a pulse stimulus paradigm according to another embodiment.
Figure 7:
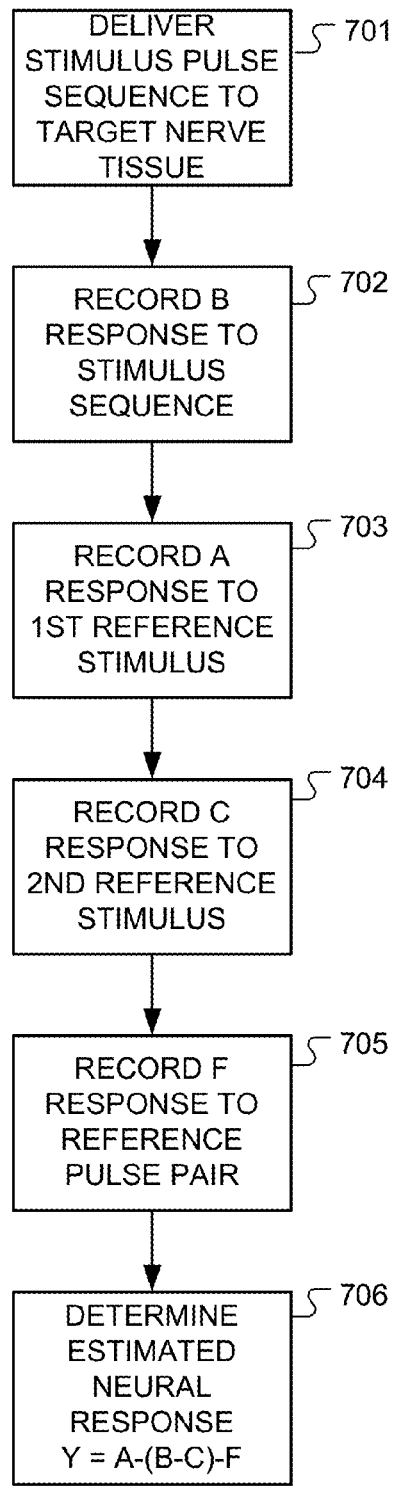
FIG. 7 shows various functional blocks in a method according to FIG. 6.

FIG. 6 shows an example of a pulse stimulus paradigm and FIG. 7 shows various functional blocks in a method according to another embodiment. First, a response stimulation pulse sequence is delivered delivering to the target nerve tissue, step 701, that includes delivering a first stimulus pulse P1 to elicit a corresponding action potential in the target nerve tissue, followed by a relative refractory period and within the relative refractory period, delivering to the target nerve tissue a second stimulus pulse P2 and an associated acoustic stimulation signal. The acoustic stimulation signal may precede or follow the second stimulus pulse P2. A recording is made of a B response by target nerve tissue to the stimulus pulse sequence, step 702. A recording is also made of an A response by the target nerve tissue to delivery of a first reference stimulus pulse P7 corresponding to the second stimulus pulse P2 and the associated acoustic stimulation signal, step 703. A recording also is made of a C response by the target nerve tissue to delivery of a second reference stimulus pulse P5 corresponding to the first stimulus pulse P1, step 704. And a recording is made of an F response with a pair of reference stimulus pulses P8 and P9 associated with the first and second stimulus pulses P1 and P2, step 705. The recorded responses are processed, step 706, to determine an artifact canceled estimated neural response Y following the relation Y=A−(B−C)−F.

Embodiments of the invention may be implemented in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of determining an estimated neural response in a hybrid acoustic-electrical audio prosthesis comprising:
    recording a B response by target nerve tissue to a first hybrid electric acoustic stimulus sequence which includes:
        i. delivering to the target nerve tissue a first electric stimulus pulse P1 without acoustic stimulation to elicit a corresponding action potential followed by a relative refractory period, and
        ii. after the relative refractory period, delivering to the target nerve tissue a second electric stimulus pulse P2 and an associated acoustic stimulation signal;
    recording an E response by the target nerve tissue to a second electric stimulus sequence without acoustic stimulation which includes:
        i. delivering to the target nerve tissue a third electric stimulus pulse P3 without acoustic stimulation to elicit a corresponding action potential followed by a relative refractory period, and
        ii. within the relative refractory period, delivering to the target nerve tissue a fourth electric stimulus pulse P4 without acoustic stimulation;
    recording a C response by the target nerve tissue to delivery of a first reference electric stimulus pulse P5 without acoustic stimulation corresponding to the first electric stimulus pulse P1;
    recording a D response by the target nerve tissue to delivery of a second reference electric stimulus pulse P6 without acoustic stimulation corresponding to the third electric stimulus pulse P3;
    processing the recorded responses to determine an artifact canceled estimated neural response Y following the relation $Y=(B-C)-(E-D)$.

2. A method according to claim 1, wherein the acoustic stimulation signal is triggered by the second electric stimulus pulse P2.

3. A method according to claim 1, wherein the acoustic stimulation signal precedes the second electric stimulus pulse P2.

4. A method according to claim 1, wherein the acoustic stimulation signal follows the second electric stimulus pulse P2.

5. A method according to claim 1, wherein the electric stimulus pulses have substantially equal amplitudes.

6. A neural response measurement system comprising:
    a non-transitory computer readable medium programmed with instructions to determine an estimated neural response in a hybrid acoustic-electrical prosthesis, comprising the steps of:
    recording a B response by target nerve tissue to a first hybrid electric stimulus sequence which includes:
        i. delivering to the target nerve tissue a first electric stimulus pulse P1 without acoustic stimulation, to elicit a corresponding action potential followed by a relative refractory period, and
        ii. after the relative refractory period, delivering to the target nerve tissue a second electric stimulus pulse P2 and an associated acoustic stimulation signal;
    recording an E response by the target nerve tissue to a second electric stimulus sequence without acoustic stimulation which includes:
        i. delivering to the target nerve tissue a third electric stimulus pulse P3 without acoustic stimulation to elicit a corresponding action potential followed by a relative refractory period, and
        ii. within the relative refractory period, delivering to the target nerve tissue a fourth electric stimulus pulse P4 without acoustic stimulation;
    recording a C response by the target nerve tissue to delivery of a first reference electric stimulus pulse P5 without acoustic stimulation corresponding to the first stimulus pulse P1;
    recording a D response by the target nerve tissue to delivery of a second reference electric stimulus pulse P6 without acoustic stimulation corresponding to the third electric stimulus pulse P3;
    processing the recorded responses to determine an artifact canceled estimated neural response Y following the relation $Y=(B-C)-(E-D)$.

7. A system according to claim 6, wherein the acoustic stimulation signal is triggered by the second electric stimulus pulse P2.

8. A system according to claim 6, wherein the acoustic stimulation signal precedes the second electric stimulus pulse P2.

9. A system according to claim 6, wherein the acoustic stimulation signal follows the second electric stimulus pulse P2.

10. A system according to claim 6, wherein the electric stimulus pulses have substantially equal amplitudes.

* * * * *